United States Patent [19]

Immel et al.

[11] Patent Number: 5,300,706
[45] Date of Patent: Apr. 5, 1994

[54] PROCESS FOR THE PREPARATION OF D,1-MENTHOL

[75] Inventors: Otto Immel; Gerhard Darsow; Hans-Josef Buysch, all of Krefeld, Fed. Rep. of Germany

[73] Assignee: Bayer Aktiengesellschaft, Leverkusen, Fed. Rep. of Germany

[21] Appl. No.: 28,850

[22] Filed: Mar. 10, 1993

[30] Foreign Application Priority Data

Mar. 17, 1992 [DE] Fed. Rep. of Germany ....... 4208443

[51] Int. Cl.⁵ .................. C07C 29/00; C07C 29/17
[52] U.S. Cl. .................................. 568/830; 568/829
[58] Field of Search ............................. 568/829, 830

[56] References Cited

U.S. PATENT DOCUMENTS

| 2,843,636 | 7/1958 | Booth | 568/830 |
| 2,871,272 | 1/1959 | Bottoms | 568/830 |
| 3,078,316 | 2/1963 | Bottoms | 568/830 |
| 4,058,571 | 11/1977 | Biedermann | 568/830 |
| 4,943,549 | 7/1990 | Immel et al. | 502/304 |

FOREIGN PATENT DOCUMENTS

| 0351661 | 1/1990 | European Pat. Off. | |
| 2314813 | 3/1973 | Fed. Rep. of Germany | 568/830 |
| 2314813 | 9/1974 | Fed. Rep. of Germany | |
| 285403 | 9/1928 | United Kingdom | |
| 1415486 | 11/1975 | United Kingdom | |

OTHER PUBLICATIONS

*Chemical Abstracts*, vol. 105, 1986, p. 754, Abstract No. 191414; "Stereoselective Hydrogenation of Thymol".

Primary Examiner—Werren B. Lone
Attorney, Agent, or Firm—Sprung Horn Kramer & Woods

[57] ABSTRACT

A process for the preparation of d,l-menthol by catalytic hydrogenation of aromatic or partly hydrogenated cyclic compounds which have the carbon skeleton of menthol having at least one double bond and are substituted by oxygen in the 3-position relative to the methyl group, with simultaneous rearrangement of optically active or inactive stereoisomers of menthol at elevated temperature and under pressure is described. The hydrogenation, which is to be carried out continuously, is carried out on a fixed bed catalyst which comprises, as active constituents, palladium, ruthenium or rhodium or a mixture of these elements, and comprises alkali metal hydroxides and/or alkali metal sulphates as promoters; the support for this catalyst is doped with a rare earth metal and manganese.

20 Claims, No Drawings

PROCESS FOR THE PREPARATION OF D,l-MENTHOL

BACKGROUND OF THE INVENTION

1. Field of the Invention

The invention relates to a continuous process for the preparation of d,l-menthol in the presence of a fixed bed catalyst which comprises palladium, ruthenium or rhodium or a mixture of these elements as active constituents, and furthermore comprises promoters, and the support of which is doped with a rare earth metal and manganese.

The d,l-menthol prepared can be employed either in the racemic form or, after resolution of the racemate, in the form of its l - or d-antipode in the perfumes, flavourings and medicaments industry.

2. Description of the Related Art

It is known to prepare d,l-menthol by discontinuous catalytic hydrogenation of thymol and other compounds which have the carbon skeleton of menthol having at least one double bond in the 4-position and are substituted by oxygen. The preparation of d,l-menthol by racemisation and/or rearrangement of d-menthol and the optically active or inactive stereoisomers of menthol is likewise known and can be carried out, for example, by heating these compounds with hydrogen in the presence of a hydrogenation catalyst. A crude product which comprises d,l-menthol, d,l-neomenthol, d,l-isomenthol and d,l-neoisomenthol in a ratio of about 6:3:1:0.2 parts by weight, corresponding to equilibrium being established, is in general obtained here in all cases, regardless of the starting material both in the catalytic hydrogenation and in the racemisation, as a result of the epimerisation which takes place during such processes. In addition to the abovementioned stereoisomers, however, by-products such as menthone and isomenthone, and furthermore methenone and hydrocarbons, such as menthenes and menthanes are additionally formed. The formation of these by-products, which can be reduced and/or rearranged to give d,l-menthol only with difficulty, if at all, causes the considerable disadvantages of processes of the prior art of the type described; for example, about 5% of hydrocarbons which cannot be reused are obtained in the process described in U.S. Pat. No. 2,843,636.

The disadvantages described are of particular significance if attempts are made to carry out these processes, which are described only for the discontinuous procedure, continuously by separating off the d,l-menthol from the product stream by means of physical separation processes and circulating the by-products. In this procedure, these undesirable by-products become concentrated in the circulating stream very quickly such that a continuous procedure based on this process is uneconomical. It is known from German Auslegeschrift 23 14 813 that d,l-menthol can be prepared by catalytic hydrogenation of compounds which have the carbon skeleton of menthol having at least one double bond and are substituted by oxygen in the 3-position relative to the methyl group, and/or by rearrangement of optically active or inactive stereoisomers of menthol at elevated temperature and under pressure if the hydrogenation is carried out continuously using a cobalt catalyst, arranged in a fixed bed, having a manganese content of 10 to 40% by weight, based on the total amount of cobalt and manganese, the amount of hydrogen per mol of starting material being at least 10 times the amount required for hydrogenation of a benzene nucleus; this reaction is carried out in the temperature range from 170° to 220° C. and under a pressure of at least 25 bar. A cobalt catalyst having a content of 15 to 30, in particular 20 to 25% by weight of manganese is preferably used.

However, the use of the cobalt/manganese catalyst according to German Auslegeschrift 23 14 813 mentioned is industrially expensive and pollutes the environment. Moreover, the German Auslegeschrift mentioned contains no information on the mechanical stability and life of this catalyst, and this information is of decisive importance for industrial production of d,l-menthol.

SUMMARY OF THE INVENTION

There was therefore the desire to discover a long-life and ecologically acceptable catalyst which is simple to prepare and enables the process, which is known in principle, for the preparation of d,l-menthol to be carried out continuously on an industrial scale. In the context of the invention, this is achieved with a fixed bed catalyst which comprises, as active constituents, palladium, ruthenium, rhodium or a mixture of these elements, furthermore comprises alkali metal hydroxides and/or alkali metal sulphates as promoters, and the carrier of which is doped by a rare earth metal and manganese.

The invention relates to a process for the preparation of d,l-menthol by catalytic hydrogenation of compounds which have the carbon skeleton of menthol having at least one double bond and are substituted by oxygen in the 3-position relative to the methyl group, with simultaneous rearrangement of optically active or inactive stereoisomers of menthol, the amount of hydrogen per mol of starting material being at least 5 times the amount required for hydrogenation of a benzene nucleus and the reaction being carried out in the temperature range of 160° to 220° C. under a pressure of at least 25 bar, which is characterised in that the hydrogenation is carried out continuously on a fixed bed catalyst which comprises, as the active constituents, palladium, ruthenium, rhodium or a mixture of these elements, and which comprises, as promoters, one or more alkali metal hydroxides and/or alkali metal sulphates, and the support of which comprises one or more rare earth metals and manganese.

DETAILED DESCRIPTION OF THE INVENTION

Possible supports are materials comprising aluminum, such as aluminium oxides, aluminium spinels, aluminium phosphate or alumosilicates, preferably aluminium oxides, particularly preferably α- or γ-Al$_2$O$_3$. γ-Al$_2$O$_3$ is especially preferably employed as the support.

The support is doped with one or more compounds of rare earth metals and of manganese. The content of rare earth metals and manganese together is 0.05 to 8% by weight, preferably 0.2 to 5% by weight, based on the total weight of the catalyst. The weight ratio of rare earth metals to manganese is 5:1 to 1:5, preferably 2:1 to 1:2. Rare earth metals are understood as meaning the elements of sub-group III of the Periodic Table (Mendeleev), such as scandium, yttrium, lanthanum and the lanthanides. Yttrium, lanthanum, cerium, praseodymium, neodymium and dysprosium are preferably meant, particularly preferably cerium and lanthanum, and especially preferably cerium. The rare earth metals often occur in association with one another. For example, the especially preferred cerium can be associated with lanthanum, praseodymium, neodymium, dysprosium or yttrium, or with several of these. Such an association is otherwise familiar to the expert for all the rare earth metals mentioned.

The noble metals palladium, ruthenium, rhodium or a mixture of several of them, which act as active constituents, are present in a total amount of 0.05 to 5, preferably 0.05 to 4, particularly preferably 0.1 to 3% by weight, based on the total weight of the catalyst. Among the noble metals mentioned, palladium or a combination of palladium with ruthenium, rhodium or ruthenium and rhodium is preferred. In the case of a combination, the content of palladium is 10-95% by weight, preferably 15-80% by weight, particularly preferably 20-70% by weight, based on the total weight of palladium and other noble metals. In the following description, however, the term palladium always also relates to the other two noble metals or to any desired combinations of the three noble metals mentioned.

The catalysts to be employed according to the invention can be prepared by a procedure in which compounds of the rare earth metals and of manganese are applied to the support, preferably to an aluminium oxide, in the form of extrudates, pills or beads having diameters of about 2 to 10 mm. After drying, the support doped in this way is heated to 200° to 450° C. and then impregnated or sprayed with a solution of a palladium salt (or of a salt of the other noble metals or of salts of noble metal mixtures in the context of the above statements), after which a renewed drying phase follows. Compounds of the rare earth metals and of manganese can be applied to the catalyst support, for example, merely by impregnation or spraying with suitable salts of the rare earth metals and of manganese. However, compounds of rare earth metals and of manganese can also be applied by joint precipitation of a rare earth-/manganese hydroxide mixture from rare earth and manganese salts onto the support using an alkali metal hydroxide solution or ammonia, and if appropriate subsequent washing out of the soluble contents with water. Possible rare earth and manganese salts are, in particular, the sulphates, chlorides, acetates and/or nitrates of the elements mentioned. After application of the rare earth and manganese salts and if appropriate after the precipitation described and the subsequent washing out of water-soluble compounds, the support treated in this way is first dried, before it is heated to the higher temperature mentioned, for example to 200° to 450° C., preferably 250° to 430° C. This heating is carried out over a period of 1 to 120 hours. During this period, the temperature can be increased from lower to higher values in the range stated.

After the heat treatment described, the catalyst support doped in this way is impregnated with a solution comprising palladium (noble metals). A procedure can be followed here in which the palladium (the noble metals) is (are) impregnated or sprayed onto the salt, for example, in the form of aqueous solutions of the chloride, nitrate, acetate or another suitable salt, followed by drying. If appropriate, the palladium salts, for example palladium acetate, can also be dissolved in organic solvents, such as methanol, methylene chloride, acetonitrile or dioxane, and impregnated onto the support in this manner. However, before drying, the support impregnated with palladium salts can also be treated with a solution of the above-mentioned basic compounds, the palladium precipitating as the oxide or hydroxide. Drying also follows in this variant for application of palladium. However, it is also possible first to impregnate the catalyst support charged with compounds of the rare earth metals and of manganese with a solution of one of the basic compounds mentioned, subsequently to dry the support and to apply solutions of palladium salts to the catalyst support which has been pretreated in this way and rendered basic, precipitation of the palladium in the form of its oxide or hydroxide also taking place at the time of impregnation.

The catalyst to be employed furthermore comprises 1 to 6% by weight, preferably 2 to 5% by weight, based on the total weight of the catalyst, of one or more alkali metal hydroxides and/or 1 to 6% by weight, preferably 2 to 5% by weight, likewise based on the total weight of the catalyst, of one or more alkali metal sulphates. Alkali metal hydroxides are lithium hydroxide, sodium hydroxide, potassium hydroxide, rubidium hydroxide and caesium hydroxide, preferably lithium hydroxide, sodium hydroxide and potassium hydroxide, particularly preferably sodium hydroxide or potassium hydroxide. Alkali metal sulphates are lithium sulphate, sodium sulphate, potassium sulphate, rubidium sulphate and caesium sulphate, preferably lithium sulphate, sodium sulphate and potassium sulphate, particularly preferably sodium sulphate or potassium sulphate. Drying, in general at 100° to 140° C. under reduced to normal pressure (1 to 1000 mbar, preferably 10 to 500 mbar, for example under a waterpump vacuum) also follows application of the alkali metal hydroxides and/or alkali metal sulphates.

The catalyst preferably carries both hydroxides and sulphates as promoters, within the scope of the amounts mentioned.

Impregnation with the palladium (the noble metals) and the alkali metal hydroxides and/or alkali metal sulphates is carried out separately. A procedure can be followed here in which impregnation with the palladium is first effected in the manner described above, further impregnation with alkali metal hydroxides and alkali metal sulphates taking place after drying. In this treatment, the palladium is precipitated in the form of its oxide or hydroxide. Impregnation with the alkali metal hydroxides and the alkali metal sulphates can be effected separately or together. However, it is also possible first to impregnate the support with an alkali metal hydroxide solution, subsequently to dry it and to apply salts of palladium to the catalyst support which has been pretreated in this way and rendered basic, precipitation of the palladium in the form of the oxide or hydroxide also taking place at the time of impregnation. In this variant, the alkali metal sulphates can be applied together with the alkali metal hydroxide or as a final impregnation, after application of the palladium. The support is dried after each application, in the manner already described.

Instead of impregnation with the salt solutions mentioned, spraying can also take place. The working equipment required for this and the adjustment of the charging required by choosing the amount and concentration of the solutions of the substances mentioned are known in principle to the expert.

After the last drying phase, a support prepared in the manner mentioned is in principle available for the use according to the invention. Preferably, however, before being used, particularly preferably after arrangement in the hydrogenation reactor, it is activated by treatment with hydrogen at a temperature of 150° to 400° C.

The starting compounds used for the process according to the invention are known (Ullmanns Encyclopädie der technischen Chemie (Ullmann's Encyclopaedia of Industrial Chemistry), 3rd edition, Volume 17, Munich 1966, page 24/25; and U.S. Pat. No. 2,843,636). Examples which may be mentioned are: menthone, isomenthone, d- and l -menthol, d- and l-neomenthol, d- and l-isomenthol, d,l-neoisomenthol, d,l-isomenthol and thymol, preferably thymol. These compounds can be used either individually or as any desired mixtures with one another.

The process according to the invention is carried out in the gas or trickle phase with the catalyst arranged in a fixed bed. It is carried out with excess hydrogen; the amount of $H_2$ is 5 to 20 times the amount required for hydrogenation of a benzene nucleus. The process is carried out at 160° to 220° C., preferably at 160° to 210° C.; under a pressure of more than 25 bar, preferably more than 100 bar, particularly preferably more than 200 bar. The upper limit of the pressure applied is determined both by industrial and by economic considerations and is 500 bar, preferably 200-350 bar.

The hydrogenation and racemisation as well as isomerisation which take place in the process according to the invention surprisingly proceed so mildly under the reaction conditions used that the formation of unusable by-products, such as undesirable hydrocarbons, is greatly reduced in comparison with known processes.

The catalyst to be employed according to the invention can be arranged in various apparatuses which are known in principle to the expert for such purposes. The process according to the invention is advantageously carried out in tubular reactors having one or more tubes. The reaction tubes can have lengths of, for example, 2 to 20 m and internal diameters of 20 to 800 mm. The catalysts have, for example, particle sizes of 2 to 10 mm.

The process according to the invention can be carried out with or without solvents. Suitable solvents which are inert under the reaction conditions are, for example, methanol, ethanol and isopropanol.

The resulting reaction mixture comprises such a high content of d,l-menthol that it can be worked up to give this desired product by simple distillation. Not only excellent results in the hydrogenation of thymol but also excellent yields in the reaction of the other starting compounds mentioned above are obtained with the aid of the process according to the invention.

After the desired d,l-menthol has been separated off by distillation, the first runnings of the distillation can be recycled back to the reaction with the distillation bottom product, fresh starting substance being added, for example 30 to 80% by weight of thymol, based on the distillation residue, being added. The amount of starting material added advantageously corresponds to the d,l-menthol removed by distillation. The unused hydrogen in the process according to the invention can also be circulated.

EXAMPLE 1

200 g of a commercially available $\gamma$-$Al_2O_3$ having a specific surface area of 350 $m^2$/g and a bead diameter of 2 to 6 mm were impregnated with a solution which had been prepared from 12.4 g of $Ce(NO_3)_3 \cdot 6 H_2O$, 18.28 g of $Mn(NO_3)_2 \cdot 4 H_2O$ and 75 g of water. The impregnated $Al_2O_3$ was dried at 120° C. under a waterpump vacuum for 18 hours and then heat-treated at 400° C. for 3 hours.

100 g of the catalyst support thus prepared were impregnated with a solution which had been prepared from 4.16 g of Pd acetate and 30 g of dioxane. The catalyst was dried at 100° C. for 18 hours. 2% by weight of Pd, based on the total weight of the catalyst, were applied during the impregnation.

For hydrogenation of thymol, 60 ml (50 g) of the Pd catalyst were introduced into a vertically arranged pressure tube (diameter 14 mm, length 70 cm), which was heated with an oil thermostat. For activation of the catalyst, it was treated at 250° C. under 270 bar of hydrogen for 4 hours. 80 l of hydrogen/hour were let down during this operation.

Thereafter, the temperature was dropped to 180° to 190° C., and thymol and hydrogen were passed over the catalyst from the top under 270 bar. The liquid trickled over the catalyst downwards into a separator. 60 to 80 l of hydrogen per hour were let down at the top of the separator.

The throughput corresponded to a catalyst loading of 0.2 to 0.4 g of thymol/ml of catalyst x h, and was kept in this range.

The hydrogenation product was removed from the separator at regular intervals of time and analysed. This gave the following product composition as a function of the running time over a test duration of more than 1000 hours (data in % area of the gas chromatography (GC) analysis):

| Running time (h) | d,l-Menthol (% area) | d,l-Neomenthol (% area) |
| --- | --- | --- |
| 281 | 54.6 | 31.9 |
| 375 | 55.3 | 32.6 |
| 625 | 55.3 | 31.1 |
| 649 | 55.6 | 30.3 |
| 745 | 54.9 | 31.9 |
| 964 | 55.7 | 30.6 |
| 1034 | 55.1 | 25.4 |

The remainder to make up 100% comprised mainly d,l-isomenthol, d,l-neoisomenthol and menthone compounds.

No thymol was found in the hydrogenation product.

EXAMPLE 2

100 g of the catalyst prepared according to Example 1 were additionally impregnated with a solution which had been prepared from 3 g of $K_2SO_4$ and 30 g of water. The catalyst impregnated with Pd (2%) was dried at 100° C. for 18 hours.

For continuous thymol hydrogenation, a pressure tube was filled with 60 ml (51.3 g) of the catalyst thus prepared, and the procedure followed was in accordance with the procedure described in Example 1. The catalyst was first activated again at 250° C. under 270 bar, before the continuous hydrogenation of thymol was started.

The thymol throughput corresponded to a catalyst loading of 0.2 to 0.3 g/ml of catalyst x hour. 70 to 90 l per hour of hydrogen were let down from the pressurised separator. The reaction product showed the following composition (according to GC analyses) as a function of the hydrogenation temperature and the test duration.

| Running time (h) | d,l-Menthol (% area) | d,l-Neomenthol (% area) |
| --- | --- | --- |
| 90 | 54.6 | 29.6 |
| 138 | 55.6 | 31.4 |
| 162 | 55.1 | 31.6 |
| 477 | 55.5 | 30.8 |
| 547 | 55.6 | 30.5 |

No thymol was found in the hydrogenation product. The remainder to make up 100% comprised mainly d,l-isomenthol, d,l-neoisomenthol and menthone compounds.

EXAMPLE 3

400 g of a commercially available $\gamma$-Al$_2$O$_3$ having a specific surface area of 350 m$^2$/g and a bead diameter of 2-6 mm were impregnated with a solution which had been prepared from 25 g of La(NO$_3$)$_3$. 6H$_2$O, 35.7 g of Mn(CH$_3$COO)$_2$. 4H$_2$O and 80 g of water.

The aluminium oxide impregnated in this way was then dried at 100° C. under a waterpump vacuum for 18 hours and then heat-treated at 400° C. for 4 hours.

100 g of the catalyst support prepared in this way were impregnated with a solution which had been prepared from 4.16 g of Pd-acetate and 35 g of methylene chloride. The catalyst was dried at 100° C. under a waterpump vacuum for 18 hours.

60 ml (48.8 g) of the catalyst thus prepared were used for hydrogenation of thymol as in Example 1. The catalyst was first activated in a stream of hydrogen at 250° C. under 270 bar for 4 hours. The continuous hydrogenation of thymol was carried out under the same reaction conditions as in Example 1. This gave the following product composition as a function of the running time of the hydrogenation operation (data in % area of the gas chromatography analysis):

| Running time (h) | d,l-Menthol (% area) | d,l-Neomenthol (% area) | Unknown by-products (% area) |
| --- | --- | --- | --- |
| 92 | 55.1 | 29.2 | 0.2 |
| 180 | 54.1 | 28.7 | 0.2 |
| 252 | 55.7 | 28.7 | 0.1 |
| 418 | 54.6 | 28.6 | 0.2 |
| 586 | 53.9 | 28.8 | 0.2 |
| 635 | 54.2 | 31.6 | 0.2 |
| 706 | 53.9 | 32.2 | 0.2 |

The remainder to make up 100% comprised d,l-isomenthol, d,l-neoisomenthol and menthone compounds.

EXAMPLE 4

100 g of the aluminium oxide impregnated with cerium and manganese according to Example 1 were impregnated with a solution which had been prepared from 0.76 g of rhodium acetate and 35 g of methanol. After intermediate drying, the catalyst was activated in a stream of hydrogen at 400° C. for 24 hours.

60 ml (49 g) of the catalyst thus prepared were employed for continuous hydrogenation of thymol in the same manner as in Example 1. This gave the following product composition as a function of the operating hours of the catalyst (data in % area of the gas chromatography analysis):

| Running time (h) | d,l-Menthol (% area) | d,l-Neomenthol (% area) | Unknown compounds (% area) |
| --- | --- | --- | --- |
| 30 | 52.3 | 26.6 | 0.1 |
| 49 | 55.6 | 28.1 | 0.1 |
| 98 | 55.9 | 28.5 | 0.1 |
| 175 | 55.9 | 28.1 | 0.2 |
| 274 | 54.3 | 27.4 | 0.3 |

The remainder to make up 100% comprised d,l-isomenthol, d,l-neoisomenthol and menthone compounds.

EXAMPLE 5

60 ml of the rhodium catalyst prepared according to Example 4 were introduced into a pressure tube and were first activated at 300° C. under 272 bar of hydrogen for 19 hours, 100 l of hydrogen/hour being let down.

0.2 to 0.3 g of thymol/ml of catalyst x hour was then employed in the hydrogenation, carried out continuously, under about 270 bar. 80 to 100 l of hydrogen per hour were let down at the top of the separator. The hydrogenation product was removed from the separator at regular intervals of time and analysed. This gave the following product composition as a function of the running time and the reaction temperature (data in % area of the gas chromatography (GC) analysis):

| Running time (h) | Temperature (°C.) | d,l-Menthol (% area) | d,l-Neomenthol (% area) | Unknown compounds (% area) |
| --- | --- | --- | --- | --- |
| 20 | 190 | 55.1 | 28.9 | 0.1 |
| 212 | 181 | 56.2 | 28.3 | 0.1 |
| 346 | 190 | 54.6 | 29.3 | 0.3 |
| 442 | 171 | 55.0 | 28.3 | 0.2 |
| 611 | 189 | 56.4 | 28.4 | 0.1 |
| 706 | 181 | 56.4 | 28.3 | 0.2 |
| 825 | 177 | 56.4 | 28.1 | 0.1 |
| 969 | 177 | 56.0 | 27.7 | 0.1 |
| 1068 | 176 | 56.3 | 28.2 | 0.1 |
| 1186 | 177 | 56.5 | 28.3 | 0.1 |
| 1353 | 177 | 56.2 | 28.1 | 0.4 |

The remainder to make up 100% comprised d,l-isomenthol, d,l-neoisomenthol and menthone compounds.

EXAMPLE 6

100 g of the aluminium oxide impregnated with lanthanum and manganese in Example 3 were impregnated with a solution which had been prepared from 2.52 g of rhodium acetate and 35 g of water. The catalyst was dried at 100° C. under a waterpump vacuum for 18 hours, and then activated under a stream of hydrogen at 400° C. for 23 hours.

60 ml (47.2 g) of the catalyst thus prepared were employed for the continuous hydrogenation of thymol, the procedure followed being the same as in Example 3. This gave the following product composition as a function of the running time of the hydrogenation (data in % area of the gas chromatography analysis):

| Running time (h) | d,l-Menthol (% area) | d,l-Neomenthol (% area) | Unknown substances (% area) |
| --- | --- | --- | --- |
| 35 | 54.6 | 28.4 | 0.1 |

-continued

| Running time (h) | d,l-Menthol (% area) | d,l-Neomenthol (% area) | Unknown substances (% area) |
|---|---|---|---|
| 59 | 54.7 | 28.3 | 0.3 |
| 130 | 55.1 | 28.3 | 0.1 |
| 201 | 56.8 | 28.1 | 0.1 |

EXAMPLE 7

A Ru-Ce-Mn-Al$_2$O$_3$ catalyst prepared in accordance with Example 1 of EP 0 351 661 B1 was additionally impregnated with sodium hydroxide (1.8 g of NaOH/100 ml of catalyst), dried again and employed for the hydrogenation of thymol. The catalyst was activated in a stream of hydrogen at 250° C. for 3 hours.

A 250 ml shaking autoclave, equipped on the inside with a centrally mounted wire basket which was permanently connected to the autoclave and was filled with 25 ml (20.1 g) of the H$_2$-activated catalyst, was used for the hydrogenation of thymol. 50 g of thymol were hydrogenated under a hydrogen pressure of 240 to 300 bar at 180° C. using this catalyst filling. The hydrogenation time was 6.2 hours. According to gas chromatography, the hydrogenation product contained 56.2 % area of d,l-menthol.

What is claimed is:

1. A process for the preparation of d,l-menthol by catalytic hydrogenation of aromatic or partly hydrogenated cyclic compounds which have the carbon skeleton of menthol having at least one double bond and are substituted by oxygen in the 3-position relative to the menthyl group, with simultaneous rearrangement of optically active or inactive stereoisomers of menthol, the amount of hydrogen per mol of starting material being at least 5 times the amount required for hydrogenation of a benzene nucleus and the reaction being carried out in the temperature range of 160° to 220° C. under a pressure of at least 25 bar, wherein the hydrogenation is carried out continuously on a fixed bed catalyst which comprises, as the active constituents, palladium, ruthenium, rhodium or a mixture of these elements, and which comprises, as promoters, one or more members of the group consisting of alkali metal hydroxides and alkali metal sulphates, and the support of which comprises one or more rare earth metals and maganese.

2. The process of claim 1, wherein as the support, an α- or γ-Al$_2$O$_3$ is first treated with at least one compound of rare earth metals (sub-group III of the periodic table of the elements according to Mendeleev) and with at least one compound of manganese, the total amount of rare earth metals and of maganese being 0.05 to 8% by weight, based on the total weight of the catalyst, and the weight ratio of rare earth metals to manganese being 5:1 to 1:5.

3. The process of claim 2, wherein the total amount of rare earth metals and manganese is 0.2 to 5% by weight, based on the total weight of the catalyst.

4. The process of claim 2, wherein the weight ratio of rare earth metals to manganese is 2:1 to 1:2.

5. The process of claim 1, wherein the support is treated with an amount of at least one compound of palladium, ruthenium, rhodium or of a mixture of several of them such that the content of these noble metals is 0.05 to 5% by weight, based on the total weight of the catalyst.

6. The process of claim 5, wherein the content of noble metals is 0.05 to 4% by weight.

7. The process of claim 6, wherein the content of noble metals is 0.1 to 3% by weight.

8. The process of claim 1, wherein the rare earth metal employed is one or more from the group comprising yttrium, lanthanum, cerium, praseodymium, neodymium and dysprosium.

9. The process of claim 8, wherein the rare earth metal employed is one or more from the group comprising cerium and lanthanum.

10. The process of claim 9, wherein the rare earth metal employed is cerium.

11. The process of claim 1, wherein the catalyst comprises palladium or a combination of palladium/ ruthenium, palladium/rhodium or palladium/ruthenium/ rhodium, and in that in the case of a combination, the weight content of the palladium in the combination of palladium/other noble metals is 10 to 95%, based on the total weight of all the noble metals.

12. The process of claim 11, wherein the weight content of the palladium in the combination is 15 to 80%, based on the total weight of all the noble metals.

13. The process of claim 12, wherein the weight content of the palladium in the combination is 20 to 70%, based on the total weight of all the noble metals.

14. The process of claim 1, wherein the content of promoters is 1 to 6% by weight of hydroxides, 1 to 6% by weight of sulphates, or both, all the percentages by weight being based on the total weight of the catalyst.

15. The process of claim 14, wherein 2 to 5% by weight of hydroxides, 2 to 5% by weight of sulphates, or both, based on the total weight of the catalyst, are present as promoters.

16. The process of claim 1, which is carried out under a pressure of 25 to 500 bar.

17. The process of claim 16, which is carried out under a pressure of 100 to 500 bar.

18. The process of claim 17, which is carried out under a pressure of 200 to 350 bar.

19. The process of claim 1, wherein thymol is employed as the starting substance.

20. The process of claim 1, wherein the d,l-menthol is removed by distillation from the reaction product of the simultaneous hydrogenation and rearrangement, and the remaining reaction products are recycled into the reaction with addition of 30 to 80% by weight of thymol, based on the remaining reaction products.

* * * * *

UNITED STATES PATENT AND TRADEMARK OFFICE
CERTIFICATE OF CORRECTION

PATENT NO. : 5,300,706
DATED : April 5, 1994
INVENTOR(S) : Otto Immel, et al.

It is certified that error appears in the above-identified patent and that said Letters Patent is hereby corrected as shown below:

Col. 9, Line 36                          Delete "menthyl" and substitute --methyl--

Signed and Sealed this

Second Day of November, 1999

Attest:

Q. TODD DICKINSON

*Attesting Officer*          *Acting Commissioner of Patents and Trademarks*